United States Patent [19]

Kopf-Sill et al.

[11] Patent Number: 5,842,787
[45] Date of Patent: Dec. 1, 1998

[54] MICROFLUIDIC SYSTEMS INCORPORATING VARIED CHANNEL DIMENSIONS

[75] Inventors: Anne R. Kopf-Sill, Portola Valley; John Wallace Parce, Palo Alto, both of Calif.

[73] Assignee: Caliper Technologies Corporation, Palo Alto, Calif.

[21] Appl. No.: 948,194

[22] Filed: Oct. 9, 1997

[51] Int. Cl.[6] .................................................. B01F 5/00
[52] U.S. Cl. ......................... 366/340; 366/336; 366/341; 138/42; 436/180
[58] Field of Search ..................................... 366/341, 336, 366/337, 338, 339, 340; 422/81, 100; 436/52, 174, 179, 180; 435/288.4, 288.5; 204/450, 451; 138/177, 138, 140, 42

[56] References Cited

U.S. PATENT DOCUMENTS

| | | |
|---|---|---|
| 4,390,403 | 6/1983 | Batchelder . |
| 4,534,659 | 8/1985 | Dourdeville et al. .................... 366/341 |
| 4,908,112 | 3/1990 | Pace ..................................... 204/299 R |
| 5,126,022 | 6/1992 | Soane et al. . |
| 5,229,297 | 7/1993 | Schnipelsky et al. ..................... 436/94 |
| 5,252,294 | 10/1993 | Kroy et al. ............................... 422/102 |
| 5,304,487 | 4/1994 | Wilding et al. ......................... 435/291 |
| 5,376,252 | 12/1994 | Ekstrom et al. ..................... 204/299 R |
| 5,443,890 | 8/1995 | Ohman ................................... 428/167 |
| 5,498,392 | 3/1996 | Wilding et al. . |
| 5,500,071 | 3/1996 | Kaltenbach et al. . |
| 5,571,410 | 11/1996 | Swedberg et al. . |
| 5,585,069 | 12/1996 | Zanzucchi et al. . |
| 5,593,838 | 1/1997 | Zanzucchi et al. . |
| 5,603,351 | 2/1997 | Cherukuri et al. . |
| 5,635,358 | 6/1997 | Wilding et al. . |
| 5,637,469 | 6/1997 | Wilding et al. ......................... 435/7.21 |
| 5,744,366 | 4/1998 | Kricka et al. ............................. 436/63 |

FOREIGN PATENT DOCUMENTS

| | | |
|---|---|---|
| 96/04547 | 2/1996 | WIPO . |
| WO 97/02357 | 1/1997 | WIPO . |
| WO 97/38300 | 10/1997 | WIPO . |

OTHER PUBLICATIONS

Dasgupta, P.K. et al., "Electroosmosis: A Reliable fluid Propulsion System for Flow Injection Analysis," *Anal. Chem.* 66:1792–1798 (1994).

Jacobson, S.C. et al., "Fused Quartz Substrates for Microchip Electrophoresis," *Anal. Chem.* 67:2059–2063 (1995).

Manz, A. et al., "Electroosmotic pumpgin and electrophoretic separations for miniaturized chemical analysis systems," *J. Micromech. Microeng.* 4:257–265 (1994).

Ramsey, J.M. et al., "Microfabricated chemical measurement systems," *Nature Med.* 1:1093–1096 (1995).

Seiler, K. et al., "Planar Glass Chips for Capillary Electrophoresis: Repetitive Sample Injection, Quantitation, and Separation Efficiency," *Anal. Chem.* 65:1481–1488 (1993).

Seiler, K. et al., "Electroosmotic Pumping and Valveless Control of Fluid Flow within a Manifold of Capillaries on a Glass Chip," *Anal. Chem.* 66:3485–3491 (1994).

*Primary Examiner*—Tony G. Soohoo
*Attorney, Agent, or Firm*—Matthew B. Murphy

[57] ABSTRACT

The present invention is generally directed to improved microfluidic devices, systems and methods of using same, which incorporate channel profiles that impart significant benefits over previously described systems. In particular, the presently described devices and systems employ channels having, at least in part, depths that are varied over those which have been previously described. These varied channel depths provide numerous beneficial and unexpected results.

42 Claims, 6 Drawing Sheets

Figure 5B

MICROFLUIDIC SYSTEMS INCORPORATING VARIED CHANNEL DIMENSIONS

BACKGROUND OF THE INVENTION

Microfluidic devices and systems have been gaining substantial interest as they are increasingly being demonstrated to be robust, highly accurate, high throughput and low cost methods of performing previously cumbersome and or expensive analytical operations.

In particular, microfluidic systems have been described for use in ultra high throughput screening assay systems, e.g., for pharmaceutical discovery, diagnostics and the like. See International Application No. PCT/US97/10894 filed Jun. 28, 1997 (Attorney Docket No. 17646-000420PC). In addition, such microfluidic systems have reportedly been used in performing separations-based analyses, e.g., nucleic acid separations, etc. See, e.g., Woolley et al., Proc. Nat'l Acad. Sci., USA 91:11348–11352 (1994).

Despite the promise of microfluidic systems in terms of throughput, automatability and cost, many of the systems that have been described suffer from substantial drawbacks. Initially, many of these systems have substantial reductions in resolution over their counterpart methods on the bench top. In particular, a number of relatively minor considerations can readily become major factors when considered in the context of the relatively small amounts of material transported through these systems. For example, in microfluidic channels that include curves or turns, variations in distances through these turns and curves at the inside and outside edges can substantially affect the resolution of materials transported through these channels.

Further, simple operations, such as dilution and mixing have generally been accomplished at the expense of overall device volume, e.g., adding to the reagent/material volume required for carrying out the overall function of the device. In particular, such mixing typically requires much larger chambers or channels in order to provide adequate mixing of reagents or diluents within the confines f the microfluidic systems.

Thus, it would be generally desirable to provide microfluidic systems that are capable of capitalizing upon the myriad benefits described above, without sacrificing other attributes, such as resolution volume, and the like. The present invention meets these and other needs.

SUMMARY OF THE INVENTION

The present invention generally provides microfluidic devices, systems and methods of using these devices and systems. The microfluidic devices and systems generally incorporate improved channel profiles that result in substantial benefits over previously described microfluidic systems.

For example, in one embodiment, the present invention provides microfluidic devices and systems incorporating them, which devices comprise a body structure and at least a first microscale channel disposed therein. The microscale channel typically comprises at least first and second ends and at least a portion of the microscale channel having an aspect ratio (width/depth) less than 1. In preferred aspects, the devices and systems include an electrical controller operably linked to the first and second ends of the microscale channel, for applying a voltage gradient between the first and second ends, and/or are fabricated from polymeric materials.

In a related but alternate embodiment, the present invention provides microfluidic devices and systems that comprise a body structure having at least a first microscale channel disposed therein, where the microscale channel has at least one turning portion incorporated therein. In this embodiment, the turning portion of the channel comprises a varied depth across its width, where the varied depth is shallower at an outside edge of the turning portion than at an inside edge of the turning portion. Preferably, the relative depths at the inside edge and outside edge of the turning portion of the channel are selected whereby the time required for a material traveling through the turning portion at the outside edge is substantially equivalent to a time required for the material to travel through the turning portion at the inside edge.

As alluded to above, the present invention also comprises microfluidic systems that include the above described microfluidic devices in combination with an electrical control system. The electrical control system is operably coupled to the first and second ends of the first and second channels, and capable of concomitantly delivering a voltage to each of the first and second ends of the first and second channels.

BRIEF DESCRIPTION OF THE FIGURES

FIGS. 2A and 2B illustrate the distortion of material regions or plugs when transported through a typical, curved microfluidic channel. FIG. 2A illustrates distortion for a single material region, while

DETAILED DESCRIPTION OF THE INVENTION

I. General

A. Introduction

The present invention is generally directed to improved microfluidic devices, systems and methods of using same, which incorporate channel profiles that impart significant benefits over previously described systems. In particular, the presently described devices and systems employ channels having, at least in part, depths that are varied over those which have been previously described. These varied channel depths provide numerous beneficial and unexpected results.

As used herein, the term "microscale" or "microfabricated" generally refers to structural elements or features of a device which have at least one fabricated dimension in the range of from about 0.1 μm to about 500 μm. Thus, a device referred to as being microfabricated or microscale will include at least one structural element or feature having such a dimension. When used to describe a fluidic element, such as a passage, chamber or conduit, the terms "microscale," "microfabricated" or "microfluidic" generally refer to one or more fluid passages, chambers or conduits which have at least one internal cross-sectional dimension, e.g., depth, width, length, diameter, etc., that is less than 500 μm, and typically between about 0.1 μm and about 500 μm. In the devices of the present invention, the microscale channels or chambers preferably have at least one cross-sectional dimension between about 0.1 μm and 200 μm, more preferably between about 0.1 μm and 100 μm, and often between about 0.1 μm and 20 μm. Accordingly, the microfluidic devices or systems prepared in accordance with the present invention typically include at least one microscale channel, usually at least two intersecting microscale channels, and often, three or more intersecting channels disposed within a single body structure. Channel intersections may exist in a number of formats, including cross intersections, "T" intersections, or any number of other structures whereby two channels are in fluid communication.

The body structure of the microfluidic devices described herein typically comprises an aggregation of two or more separate layers which when appropriately mated or joined together, form the microfluidic device of the invention, e.g., containing the channels and/or chambers described herein. Typically, the microfluidic devices described herein will comprise a top portion, a bottom portion, and an interior portion, wherein the interior portion substantially defines the channels and chambers of the device. For example, typically, the body structure is fabricated from at least two substrate layers that are mated together to define the channel networks of the device, e.g., the interior portion. In preferred aspects, the bottom portion of the device comprises a solid substrate that is substantially planar in structure, and which has at least one substantially flat upper surface.

A variety of substrate materials may be employed as the bottom portion. Typically, because the devices are microfabricated, substrate materials will be selected based upon their compatibility with known microfabrication techniques, e.g., photoliphography, wet chemical etching, laser ablation, air abrasion techniques, LIGA, reactive ion etching (RIE), injection molding, embossing, and other techniques. The substrate materials are also generally selected for their compatibility with the full range of conditions to which the microfluidic devices may be exposed, including extremes of pH, temperature, salt concentration, and application of electric fields. Accordingly, in some preferred aspects, the substrate material may include materials normally associated with the semiconductor industry in which such microfabrication techniques are regularly employed, including, e.g., silica based substrates, such as glass, quartz, silicon or polysilicon, as well as other substrate materials, such as gallium arsenide and the like. In the case of semiconductive materials, it will often be desirable to provide an insulating coating or layer, e.g., silicon oxide, over the substrate material, and particularly in those applications where electric fields are to be applied to the device or its contents.

In particularly preferred aspects, the substrate materials will comprise polymeric materials, e.g., plastics, such as polymethylmethacrylate (PMMA), polycarbonate, polytetrafluoroethylene (TEFLON™), polyvinylchloride (PVC), polydimethylsiloxane (PDMS), polysulfone, and the like. Such polymeric substrates are readily manufactured using available microfabrication techniques, as described above, or from microfabricated masters, using well known molding techniques, such as injection molding, embossing or stamping, or by polymerizing the polymeric precursor material within the mold (See U.S. Pat. No. 5,512,131). Such polymeric substrate materials are preferred for their ease of manufacture, low cost and disposability, as well as their general inertness to most extreme reaction conditions. Again, these polymeric materials may include treated surfaces, e.g., derivatized or coated surfaces, to enhance their utility in the microfluidic system, e.g., provide enhanced fluid direction, e.g., as described in U.S. patent application Ser. No. 08/843,212, filed Apr. 14, 1997, and which is incorporated herein by reference in its entirety for all purposes.

Figure 1:
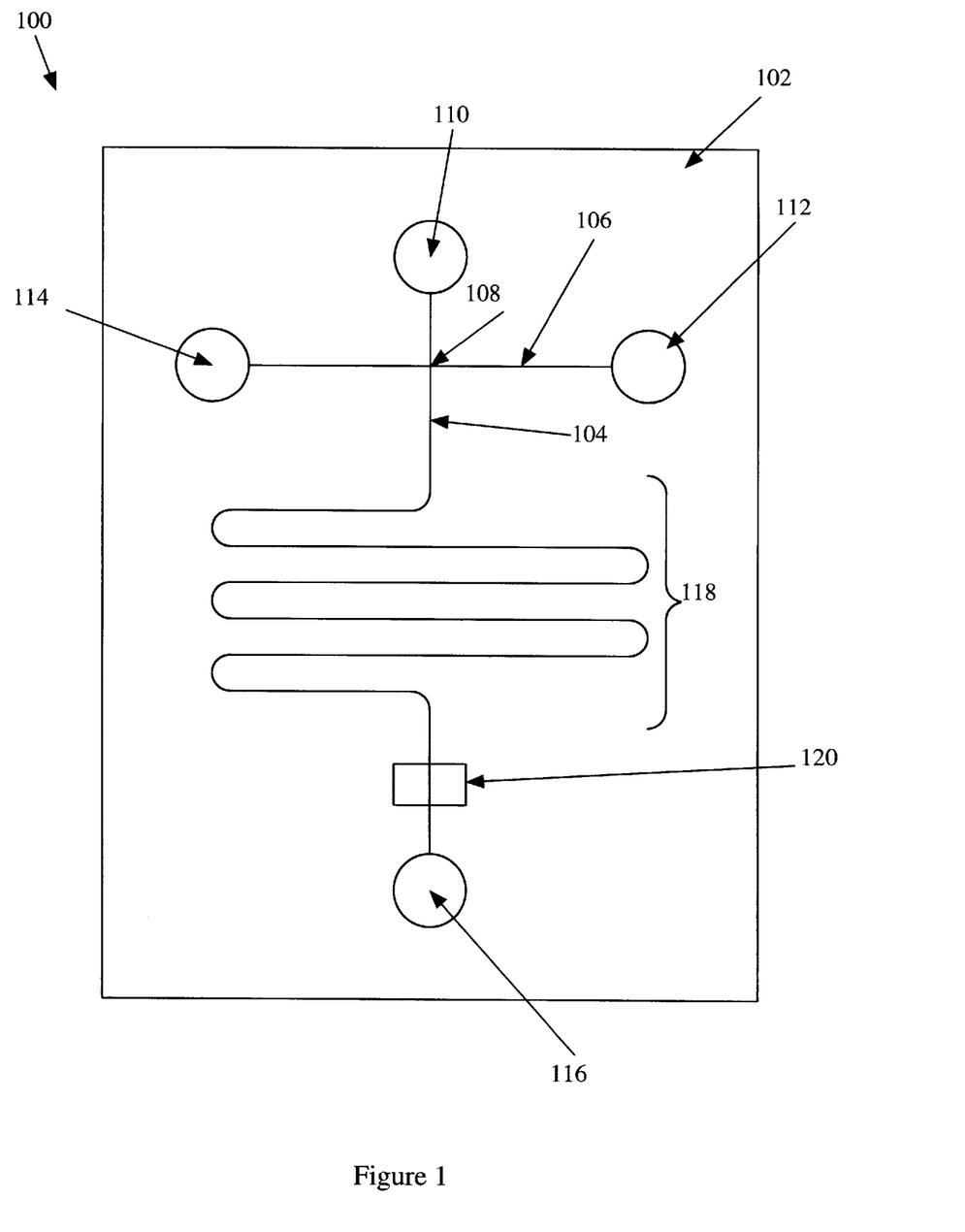
FIG. 1 schematically illustrates a microfluidic device fabricated from a planar substrate.

An example of a microfluidic device fabricated from a planar substrate is illustrated in FIG. 1. Briefly, the channels and/or chambers of the device 100 are typically fabricated into or upon a flat surface of a planar substrate 102. The channels and/or chambers of the device may be fabricated using a variety of methods whereby these channels and chambers are defined between two opposing substrates. For example, the channels, e.g. channels 104 and 106, and/or chambers of the microfluidic devices are typically fabricated into the upper surface of the bottom substrate or portion, as microscale grooves or indentations, using the above described microfabrication techniques. Alternatively, raised regions may be fabricated onto the planar surface of the bottom portion or substrate in order to define the channels and/or chambers. The top portion or substrate (not separately shown) also comprises a first planar surface, and a second surface opposite the first planar surface. In the microfluidic devices prepared in accordance with the methods described herein, the top portion also includes a plurality of apertures, holes or ports 110–116 disposed therethrough, e.g., from the first planar surface to the second surface opposite the first planar surface.

The first planar surface of the top substrate is then mated, e.g., placed into contact with, and bonded to the planar surface of the bottom substrate, covering and sealing the grooves and/or indentations in the surface of the bottom substrate, to form the channels and/or chambers (i.e., the interior portion) of the device at the interface of these two components. The holes 110–116 in the top portion of the device are oriented such that they are in communication with at least one of the channels, e.g., 104 or 106, and/or chambers formed in the interior portion of the device from the grooves or indentations in the bottom substrate. In the completed device, these holes 110–116 function as reservoirs for facilitating fluid or material introduction into the channels or chambers of the interior portion of the device, as well as providing ports at which electrodes may be placed into contact with fluids within the device, allowing application of electric fields along the channels of the device to control and direct fluid transport within the device. As shown, channel 104, which serves as the main or analysis channel in the device shown, intersects channel 106, which serves as a sample introduction channel, at intersection 108. The analysis channel 104, also includes a serpentine portion 118, which serves to extend the length of the analysis channel without requiring substantially greater substrate area.

In many embodiments, the microfluidic devices will include an optical detection window 120 disposed across one or more channels and/or chambers of the device. Optical detection windows are typically transparent such that they are capable of transmitting an optical signal from the channel/chamber over which they are disposed. Optical detection windows may merely be a region of a transparent cover layer, e.g., where the cover layer is glass or quartz, or a transparent polymer material, e.g., PMMA, polycarbonate, etc. Alternatively, where opaque substrates are used in manufacturing the devices, transparent detection windows fabricated from the above materials may be separately manufactured into the device.

These devices may be used in a variety of applications, including, e.g., the performance of high throughput screening assays in drug discovery, immunoassays, diagnostics, nucleic acid analysis, including genetic analysis, and the like. As such, the devices described herein, will often include multiple sample introduction ports or reservoirs, for the parallel or serial introduction and analysis of multiple samples, e.g., as described in U.S. patent application Ser. No. 08/845,754, filed Apr. 25, 1997, and incorporated herein by reference. Alternatively, these devices may be coupled to a sample introduction port, e.g., a pipettor, which serially introduces multiple samples into the device for analysis. Examples of such sample introduction systems are described in e.g., U.S. patent application Ser. Nos. 08/761,575 and 08/760,446 (Attorney Docket Nos. 17646-000410 and 17646-000510, respectively) each of which was filed on Dec. 6, 1996, and is hereby incorporated by reference in its entirety for all purposes.

II. Channel Aspect Ratios

In a first aspect, the present invention provides microfluidic devices and systems that comprise a body structure which has disposed therein, at least one microscale channel or channel portion, which channel or channel portion has an aspect ratio that is substantially the inverse of previously described microscale channels.

In particular, microscale channels which have been described for use in microfluidic systems, typically have employed channel dimensions in the range of from about 50 to about 200 μm wide and from about 5 to about 20 μm deep. In any event, the aspect ratios of these channels (width/depth) is well in excess of 2 and typically is in the range of from about 7 to about 10. These aspect ratios have likely resulted, at least in part, from the processes involved in the fabrication of microfluidic systems, and particularly, the microscale channels incorporated therein. Specifically, such channels are often fabricated in silicon based substrates, such as glass, quartz, silicon, etc., using photolithographic techniques. The chemistries involved in such techniques are readily used to fabricate channels having widths and depths in the above-described ranges. However, because these techniques involve etching processes, i.e., using generally available isotropic etching chemicals e.g., hydrofluoric acid (HF), they are generally not as effective in producing channels having depths substantially greater than those described, due to the increased etching time required. Specifically, isotropic agents typically etch uniformly in all directions on amorphous substrates, i.e., glass. In such instances, it becomes effectively impossible to produce channels having aspect ratios less than 1.

Microfluidic devices incorporating the above-described dimensions and aspect ratios, have proven very useful in a wide variety of important analytical applications. These applications include high-throughput screening of pharmaceutical and other test compounds (See commonly assigned U.S. application Ser. No. 08/761,575, filed Dec. 6, 1996), nucleic acid analysis, manipulation and separation (See commonly assigned U.S. application Ser. Nos. 08/835,101 and 08/845,754, filed Apr. 4, 1997 and Apr. 25, 1997, respectively), and more.

Despite the substantial utility of these systems, the present inventors have identified some potential shortcomings of microscale channels having the above-described dimensions, particularly where it is desired to transport a given material region over a substantial distance within these channels.

In a first particular example, because microfluidic systems are typically fabricated within body structures that have relatively small areas, it is generally desirable to maximize the use of the space within the body structure. As such, channels often incorporate geometries that include a number of channel turns or corners, e.g., serpentine, saw-tooth etc. The incorporation of such channel turns can have adverse effects on the ability of discrete material regions to maintain their cohesion. In particular, in a turning microscale channel, material travelling along the outside edge traverses the turn much more slowly than material travelling at the inside edge, imitating a "race-track" effect. This effect is at least in part due to the greater distance, or in the case of a three dimension fluidic system, the greater volume a material must travel through at the outside edge of a channel as opposed to the inner edge of the channel. This difference in traversal time can result in a substantial perturbation or distortion of a discrete, cohesive material plug or region in a microscale channel.

Figure 2A:
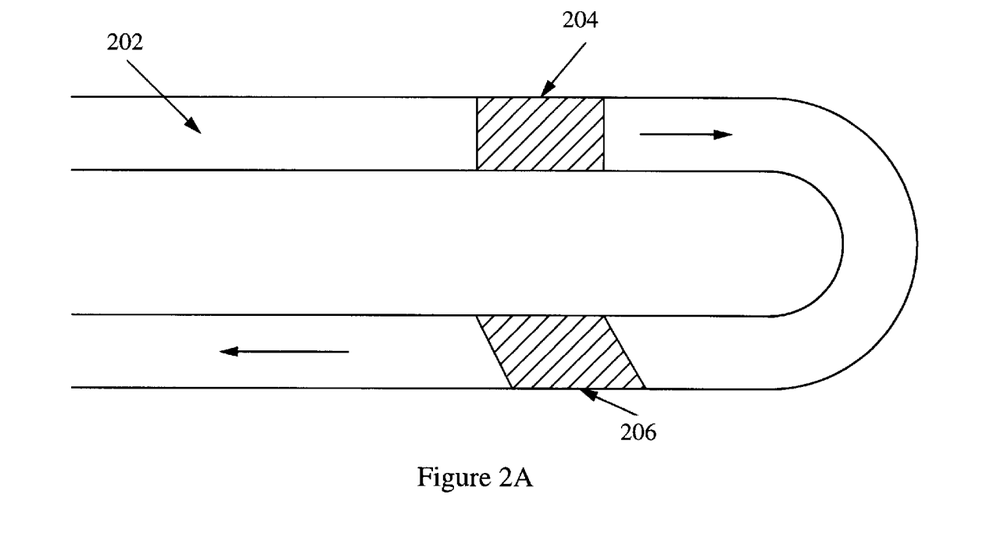

A schematic illustration of this sample perturbation resulting from turns or curves in microscale channels is provided in FIG. 2A. Briefly, FIG. 2A illustrates a discrete material region 204, e.g., a sample plug, species band or the like, travelling through a microscale channel 202. In the straight portions of the channel, the material region substantially maintains its shape with a certain level of diffusion. However, once the material region travels around a curve in the channel, the differences in flow rate through the channel at different points across the channel's width, result in a distorted material region 206.

Figure 2B:
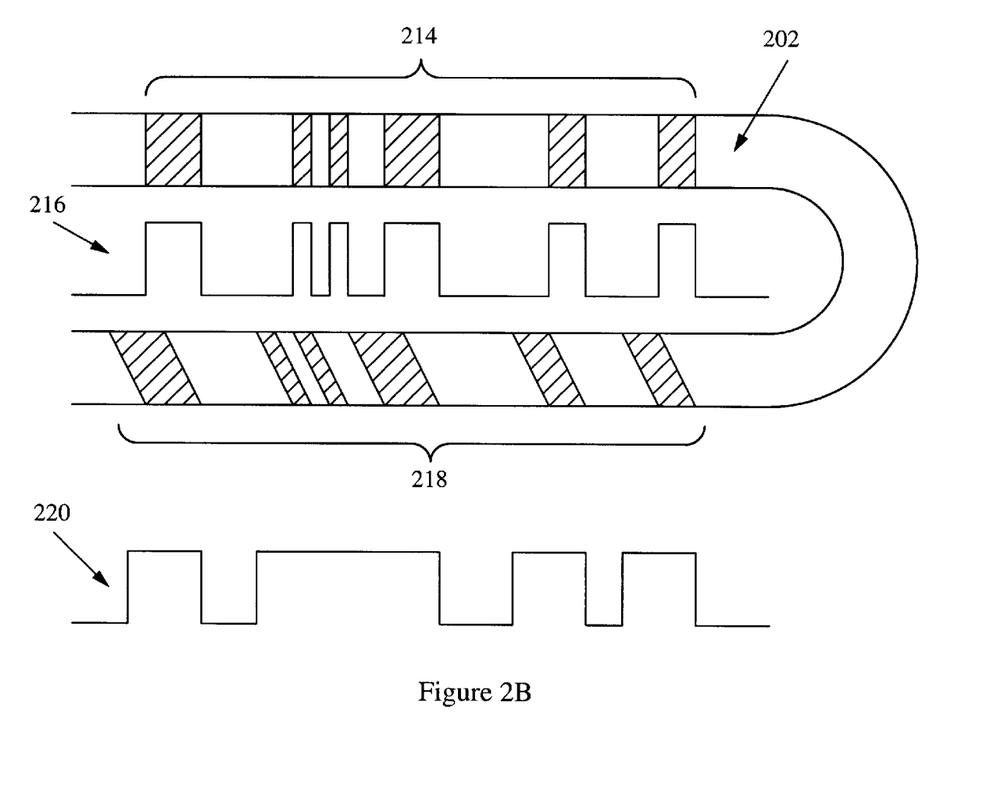
FIG. 2B illustrates distortion for multiple separate species regions or bands, such as in electrophoretic separations analysis, as well as exemplary signal, e.g., fluorescent signal that would be obtained from such species bands, both before and after the distorting effects of the channel curves.

The distortion of these material regions can adversely effect the resolution with which the particular material region is transported through the turning channel. This is particularly problematic, for example, in separation applications, e.g., protein or nucleic acid electrophoresis, where the goal is to separate a given material into its constituent elements, and to separately detect those elements. Further, such separation applications typically require substantially longer separation channels or columns, thereby increasing the number of channel turns to which a particular material will be subjected. This separate detection typically requires that the elements be maintained as well resolved material regions. FIG. 2B illustrates an exemplary separation channel incorporating a channel turn. The separated species bands 214 substantially maintain their shape and separation within the straight portions of channel 202. The well-resolved character of the species bands 214 is illustrated by the signal graph 216. After having traveled through the curved section of the channel, the species bands 218 show substantial distortion. Further, as indicated by the signal graph 220, the resolution of these bands, and thus their detectability, is substantially reduced.

This material region distortion, or sample perturbation, also becomes a problem where one wishes to separately transport materials through a microfluidic system, e.g., for separate analysis. Examples of such applications include high-throughput experimentation, e.g., screening, diagnostics, and the like. In particular, maintaining different materials, e.g. samples, as well-resolved plugs of material, i.e., without the above-described distortion effects, allows multiple plugs to be moved through a system without fear of intermixing. This also prevents the excess, uncontrolled dilution of those samples, resulting from the distortion effects.

In certain preferred aspects, the microfluidic devices and systems described herein, employ electrokinetic material transport systems for moving and directing material through and among the microscale channel networks that are incorporated in the microfluidic devices. Unfortunately, however, the level of sample perturbation is substantially increased in microfluidic systems that employ such electrokinetic material transport.

As used herein, "electrokinetic material transport systems" include systems which transport and direct materials within an interconnected channel and/or chamber containing structure, through the application of electrical fields to the materials, thereby causing material movement through and among the channel and/or chambers, i.e., cations will move toward the negative electrode, while anions will move toward the positive electrode.

Such electrokinetic material transport and direction systems include those systems that rely upon the electrophoretic mobility of charged species within the electric field applied to the structure. Such systems are more particularly referred to as electrophoretic material transport systems. Other electrokinetic material direction and transport systems rely upon the electroosmotic flow of fluid and material within a channel or chamber structure which results from the application of an electric field across such structures. In brief, when a fluid is placed into a channel which has a surface bearing charged functional groups, e.g., hydroxyl groups in etched glass channels or glass microcapillaries, those groups can ionize. In the case of hydroxyl functional groups, this ionization, e.g., at neutral pH, results in the release of protons from the surface and into the fluid, creating a concentration of protons at near the fluid/surface interface, or a positively charged sheath surrounding the bulk fluid in the channel. Application of a voltage gradient across the length of the channel, will cause the proton sheath to move in the direction of the voltage drop, i.e., toward the negative electrode.

"Controlled electrokinetic material transport and direction," as used herein, refers to electrokinetic systems as described above, which employ active control of the voltages applied at multiple, i.e., more than two, electrodes. Rephrased, such controlled electrokinetic systems concomitantly regulate voltage gradients applied across at least two intersecting channels. Controlled electrokinetic material transport is described in Published PCT Application No. WO 96/04547, to Ramsey, which is incorporated herein by reference in its entirety for all purposes. In particular, the preferred microfluidic devices and systems described herein, include a body structure which includes at least two intersecting channels or fluid conduits, e.g., interconnected, enclosed chambers, which channels include at least three unintersected termini. The intersection of two channels refers to a point at which two or more channels are in fluid communication with each other, and encompasses "T" intersections, cross intersections, "wagon wheel" intersections of multiple channels, or any other channel geometry where two or more channels are in such fluid communication. An unintersected terminus of a channel is a point at which a channel terminates not as a result of that channel's intersection with another channel, e.g., a "T" intersection. In preferred aspects, the devices will include at least three intersecting channels having at least four unintersected termini. In a basic cross channel structure, where a single horizontal channel is intersected and crossed by a single vertical channel, controlled electrokinetic material transport operates to controllably direct material flow through the intersection, by providing constraining flows from the other channels at the intersection. For example, assuming one was desirous of transporting a first material through the horizontal channel, e.g., from left to right, across the intersection with the vertical channel. Simple electrokinetic material flow of this material across the intersection could be accomplished by applying a voltage gradient across the length of the horizontal channel, i.e., applying a first voltage to the left terminus of this channel, and a second, lower voltage to the right terminus of this channel, or by allowing the right terminus to float (applying no voltage). However, this type of material flow through the intersection would result in a substantial amount of diffusion at the intersection, resulting from both the natural diffusive properties of the material being transported in the medium used, as well as convective effects at the intersection.

In controlled electrokinetic material transport, the material being transported across the intersection is constrained by low level flow from the side channels, e.g., the top and bottom channels. This is accomplished by applying a slight voltage gradient along the path of material flow, e.g., from the top or bottom termini of the vertical channel, toward the right terminus. The result is a "pinching" of the material flow at the intersection, which prevents the diffusion of the material into the vertical channel. The pinched volume of material at the intersection may then be injected into the vertical channel by applying a voltage gradient across the length of the vertical channel, i.e., from the top terminus to the bottom terminus. In order to avoid any bleeding over of material from the horizontal channel during this injection, a low level of flow is directed back into the side channels, resulting in a "pull back" of the material from the intersection.

In addition to pinched injection schemes, controlled electrokinetic material transport is readily utilized to create virtual valves which include no mechanical or moving parts. Specifically, with reference to the cross intersection described above, flow of material from one channel segment to another, e.g., the left arm to the right arm of the horizontal channel, can be efficiently regulated, stopped and reinitiated, by a controlled flow from the vertical channel, e.g., from the bottom arm to the top arm of the vertical channel. Specifically, in the 'off' mode, the material is transported from the left arm, through the intersection and into the top arm by applying a voltage gradient across the left and top termini. A constraining flow is directed from the bottom arm to the top arm by applying a similar voltage gradient along this path (from the bottom terminus to the top terminus). Metered amounts of material are then dispensed from the left arm into the right arm of the horizontal channel by switching the applied voltage gradient from left to top, to left to right. The amount of time and the voltage gradient applied dictates the amount of material that will be dispensed in this manner.

Although described for the purposes of illustration with respect to a four way, cross intersection, these controlled electrokinetic material transport systems can be readily adapted for more complex interconnected channel networks, e.g., arrays of interconnected parallel channels.

In order to provide the necessary voltage gradients to the various ports or reservoirs of a microfluidic device, e.g., as described above, the microfluidic systems generally include electrical controllers which include a plurality of electrical leads that are operably coupled to the separate ports of the microfluidic device, e.g., in electrical connection. The electrical controller is then capable of separately delivering a voltage to each of the different leads and ports. Examples of a particularly preferred electrical controller is described in, e.g., International Patent Application No. PCT/US97/12930, filed Jul. 3, 1997, and incorporated herein by reference in its entirety.

Figure 3:
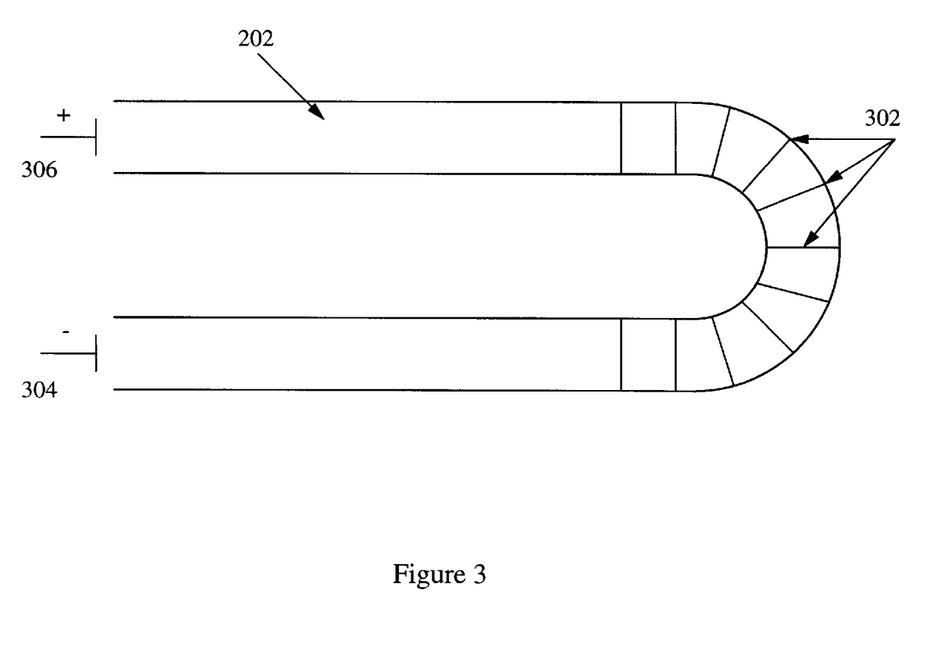
FIG. 3 illustrates a diagram of an electric field applied across the length of a turning microscale channel.

As noted above, in microfluidic systems employing electrokinetic material transport, sample perturbation around channel turns can be somewhat exacerbated. In particular, the causes of the differential rate at which materials at the inside and outside edges travel around the turn are two-fold. Initially, materials at the outside edge, as described above, must travel farther than materials at the inside edge of a turning channel and thus will take longer to traverse a turn. In addition and perhaps more importantly, under electrokinetic material transport, the movement of material is dictated by the nature of the electric field being applied across the region through which that material travels. Specifically, materials move in relation to the amount and direction of electric current. The nature of this electric field/current is substantially different at the inner edge of the turning channel than at the outer edge of the channel. A schematic illustration of the electric field that exists at such channel turns is shown in FIG. 3. In brief, within curving or turning channel 102, the electric field, e.g., as applied by negative and positive electrodes 304 and 306, respectively, is much more concentrated at the inner edge of the channel versus the outer edge of the channel, as shown by the constant voltage lines 302 across the channel. The electric field is higher where the voltage lines are closer together The differences at the inner and outer edges of the channel can be reduced by making the turning channel narrower, and thus reducing the difference in the radii of these two edges. By reducing the difference in the radii of these two edges, one proportionally reduces the difference in volume through which materials at these two edges must travel. However, this solution also requires a narrowing of the channel around the corner, resulting in increased resistance through the channel, lower throughput, and all the associated consequences, i.e., increased current heating, higher pressures, etc.

The present invention addresses the difficulties associated with the problems of turning channels, by providing channels that are narrower in width, thereby reducing differences in the volume through which the materials must travel at the inner and outer edges of a channel, but which channels are substantially deeper, thereby preventing increases in resistance or pressure. Specifically, and as noted above, the present invention provides microfluidic devices and systems having microscale channels, wherein at least a portion of the channel or channels is deeper and narrower than previously described, in order to mitigate some of the problems that have been encountered in microfluidics. In addition, by providing these channels as deeper regions, the difference in volumes through which material must travel at the inner and outer edges, becomes a smaller percentage of the overall volume of the channel around the curve, and thus has a smaller effect on the differential flow rate of material travelling at these different edges.

In particular, the present invention provides microfluidic devices and systems wherein one or more microscale channels contained within the devices and systems include channel regions having an aspect ratio of less than 1. As used herein, the term "aspect ratio," refers to the ratio of a channel's width to that channel's depth. Thus, a channel having an aspect ratio of less than 1, is deeper than it is wide, while a channel having an aspect ratio greater than 1 is wider than it is deep.

Figure 4:
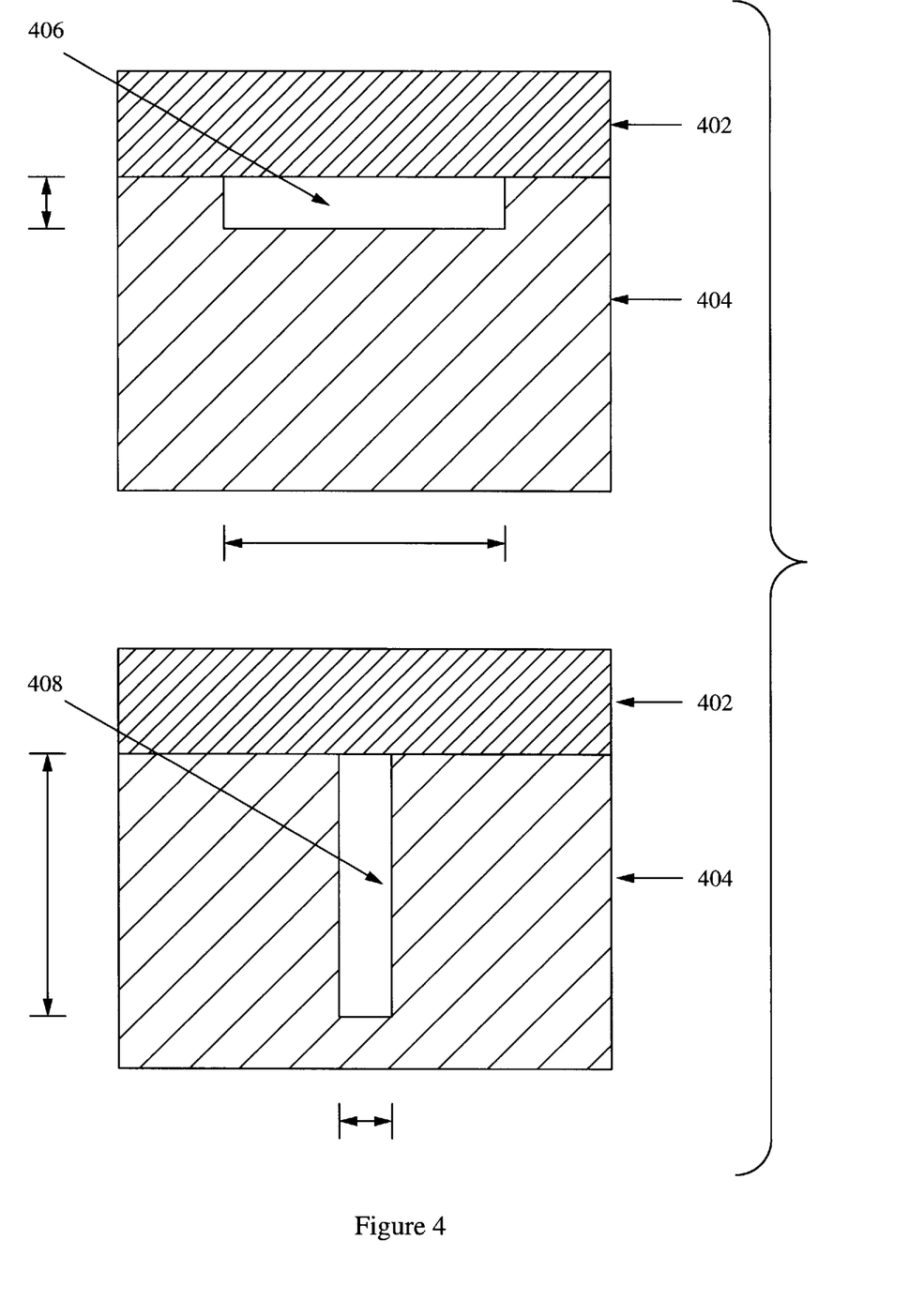
FIG. 4 illustrates a comparison of a channel having a shallow aspect ratio, e.g., >1 (width/depth)(top), as well as a channel having a deep aspect ratio, e.g., <1 (width/depth) (bottom).

Typically, the channel portions described herein, will be in the range of from about 5 to about 50 μm wide, while being from about 20 to about 200 μm deep. In preferred aspects, the aspect ratio of these channel portions will be less than or equal to about 0.5, e.g., more than twice as deep as it is wide, more preferably, about 0.2, and often in the range of about 0.1 or less. A comparison of shallow aspect ratio channels, e.g., those having an aspect ratio greater than 1 (width/depth) is shown in FIG. 4 (top), where the channel 406 is shown from an end-on perspective, fabricated into a lower substrate 404, which has been mated or bonded with upper substrate 402, to define the channel. In the bottom panel, a channel 408 is illustrated from the same perspective, but where the channel has an aspect ratio less than 1 (width/depth). As shown, both channels 406 and 408 have the same cross-sectional area, so as not to affect the level of material flow or current flow (resistance) through the channel.

Fabrication of microfluidic systems that incorporate the aspect ratios described herein, may generally be carried out using the above-described microfabrication methods. For example, crystalline substrates may be used that etch nonisotropically, and in which channels having appropriate aspect ratios are fabricated. Preferably, however, the microfluidic systems described herein are fabricated in polymeric substrates, as described above. Fabrication techniques used with polymeric substrates, e.g., injection molding, embossing, laser ablation and the like, permit the more rapid formation of substrates with appropriate depth dimensions, e.g., using LIGA methods in combination with computer aided design (CAD). Further, in the case of molding methods, the molds used to fabricate these polymeric substrates are generally fabricated from materials that are more easily manufactured, e.g., crystalline substrates, such as silicon or photoresists, permitting the use of methods capable of producing much deeper aspect ratios, e.g., LIGA methods. For example, etching positive molds using UV or x-ray etching in photoresist, or reactive ion etching directly in solid substrates such as glass or silicon, permits the production of channels having deep, straight etch profiles. These molds are then used to create negative electroforms, e.g., nickel electroforms, which in turn, are used to cast or injection mold polymeric substrates. Using such methods, aspect ratios of less than 0.02 (width/depth) are readily realized. In the case of forming polymeric substrates for use in accordance with the present invention, aspect ratios of 0.1, 0.2, 0.25, 0.3 and the like are readily achieved. Further, masters incorporating negative structures having these aspect ratios, e.g., raised ridges corresponding to the channels of the eventual device/substrate, typically provide more durable masters for use in the injection molding or casting processes.

In addition to the foregoing advantages, bonding of substrate layers also is facilitated in channels having aspect ratios described herein. In particular, in polymeric substrate based microfluidic devices incorporating previous aspect ratios, e.g., from about 2 to about 10, the upper interior wall surface on a given channel provided a substantial percentage of the overall interior surface of the channel, e.g. from about ⅓ to about ½ of the overall interior surface. Variations of this upper surface resulting from the bonding process have substantial adverse effects upon the nature of material transport within the channel. Such variations include the presence of adhesives used in the bonding process, on the upper interior surface, or in the case of thermal or solvent bonding processes, melting of the upper surface. This melting can cause variations or distortions within the upper surface, or to the channel shape, at or near the upper surface. All of these variations can potentially cause distorted flow characteristics in a microfluidic channel.

In accordance with the present invention, this upper interior surface makes up a substantially reduced proportion of the overall interior surface of the channel, e.g., less than ¼ of the overall interior surface. As such, any adverse effects resulting therefrom are also substantially reduced.

As noted above, the microfluidic devices described herein, e.g., having aspect ratios less than 1, are particularly useful in those devices which include channels having one, two, three, four, five, six or more corners, turns, etc. As used herein, the term "turn" or "corner" when referring to a channel geometry, refers to a channel having a direction change of at least 30°. Further, the term "turn" does not necessarily require an abrupt direction change, but also encompasses curved or arced channel turns. Typically, such turns or corners will be at least 45°, while preferred microfluidic devices will include channels that incorporate turns of greater than 90° and often greater than 150°. Often, as is the case of serpentine channel structures, a single channel will incorporate several turns, e.g., 2, 3, 4 or more, that are as large as 180°.

The microfluidic devices described herein may include the aspect ratios described, e.g., less than 1, with respect to all channels contained within a particular device, e.g., one or more intersecting channels, some of these channels, a single channel and even a portion or portions of one or more channels. For example, in channel structures that incorporate turns, only that portion of the channel at the turn may include such an aspect ratio. Specifically, channels may be provided having a more typical aspect ratio, e.g., greater than 2, in those portions where the channel is straight. However, at the turns, the aspect ratio is varied to less than 1. Preferably, however, the entire channel will have an aspect ratio of less than 1.

As noted above, the problems of sample perturbation are particularly troubling in those applications where one is transporting a material through relatively long turning channels, and particularly where one is desirous of maintaining that material as a well resolved region, plug or species band, as it travels through that system. Accordingly, the microfluidic devices and systems described herein, e.g., having a channel, which includes at least a channel portion having an aspect ratio of less than about 1, are particularly useful in microfluidic systems that employ such elongated channels. Such elongated channels are particularly useful in separation based analyses, e.g., separating a mixture of components into several discrete species bands, such as nucleic acid separations, protein separations, etc., where longer channels provide greater separation, e.g., greater numbers of theoretical plates.

Thus, in at least one embodiment, the microfluidic devices and systems described herein include a separation channel having an aspect ratio that is less than 1. In particular, separation channels typically gain resolution with increasing length. As such, these separation channels typically include one or more turns, and preferably include a repeating serpentine geometry. Typically, such separation channels will also include a separation matrix disposed therein. Separation matrices suitable for microfluidic systems are generally commercially available, i.e., GeneScan™ polymers available from Applied Biosystems/PerkinElmer, and the like.

The separation channel may be the main or only channel within the microfluidic device. However, in preferred aspects, the separation channel is in fluid communication with, e.g., intersects, at least one additional channel disposed within the microfluidic system, typically a sample introduction channel. In preferred aspects, a number of distinct sample introduction channels are provided in fluid communication with the separation channel, thus allowing analysis of multiple samples within a single device. Examples of particularly preferred channel geometries for carrying out separation based analyses are described in commonly assigned and co-pending U.S. application Ser. No. 08/845,754, filed Apr. 25, 1997 incorporated herein by reference in its entirety for all purposes.

III. Mixing/Dilution in Microscale Channels

A second example of problems encountered in microfluidic systems relates to the intermixing of different materials within microscale channel structures. In most instances, mixing of different materials, fluids or species, e.g., from two or more different sources, in a microfluidic system, is typically carried out by diffusional mixing of those materials within a microscale channel. Specifically, where it is desired to mix two materials, e.g., fluids, to perform a given analysis, synthesis, etc., each of the two materials is introduced, simultaneously into a microscale channel. However, even at the extremely small dimensions of these microscale channels, substantially complete diffusional mixing of discretely introduced materials requires a certain amount of time, which can vary depending upon the medium, the molecular size of the materials, e.g., the diffusion constants, and the like. Because reactions within microfluidic systems often are carried out "on the fly," within flowing channels, the channels in which these materials are to be mixed are generally provided having a sufficient length, in order to provide the materials with adequate time for substantially complete diffusional mixing. This results in channel structures that devote a large amount of channel length, and thus substrate area, to mixing applications. As used herein, the phrase "substantially complete diffusional mixing" refers to the mixing of two or more materials by diffusion, to form a substantially homogenous mixture of these materials.

The present invention, addresses this problem of microfluidic systems by providing deeper channel regions within the system, to permit adequate diffusional mixing within a shorter channel length. In particular, it takes longer for a given volume of material to travel through a deeper channel, assuming the same volume flow rate. This provides more time for materials to mix. In addition, and perhaps more importantly, the diffusion characteristics within these deeper channels are substantially enhanced. This is evident whether one introduces two or more volumes of material, serially, or in parallel into the mixing channel. Specifically, because diffusional mixing of two adjacent material regions, e.g. in a channel, is largely dictated by lateral diffusion of the material between two material regions, by providing those regions as thinner layers, either in a serial or parallel orientation, one can substantially enhance the rate at which the two layers will substantially completely diffuse together.

Figure 5A:
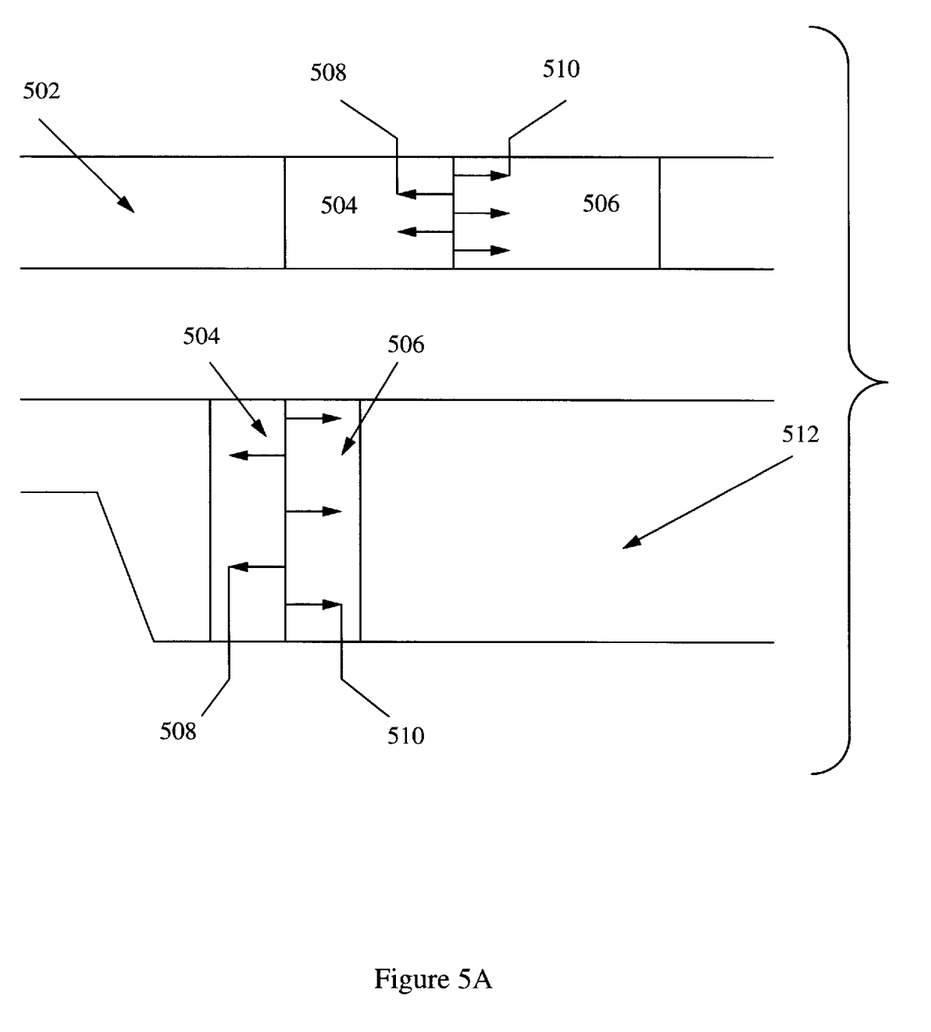
FIGS. 5A and 5B illustrate microscale channels having a varied depth to permit improved material intermixing.

The enhanced mixing of serially introduced materials within deeper channels is schematically illustrated in FIG. 5A. In particular, two materials 504 and 506 serially introduced into a shallow channel 502 will diffuse at a diffusion rate that depends upon the viscosity of the medium, the molecular size of the materials, etc., as indicated by arrows 508 and 510. In a deeper channel portion 512, however, the same diffusional kinetics, as shown by arrows 508 and 510, result in more complete diffusional mixing at a much faster rate, as the material must diffuse a much shorter distance, and has a greater interfacial area across which to diffuse. While similar advantages are also gained in such serial systems, by providing a wide mixing channel (as opposed to a deep channel), one utilizes a substantially greater amount of substrate area.

By providing deeper and narrower mixing channels, one enhances the diffusional mixing of materials, without increasing the amount of hydrodynamic flow relative to the electroosmotic flow, or altering the level of electrical resistance through that channel. In particular, the area along which the adjacent material regions interface in the mixing channel is substantially increased relative to the thickness of each region. This permits the more efficient intermixing, as described. However, by maintaining at least one thin dimension within the mixing channel (typically width), or within all other channels of the microfluidic device, there is little or no increase in hydrodynamic flow effects within these channels. Alternatively, mixing channels can be narrowed to provide enhanced mixing kinetics from materials being transported in on either side of the channel. In such instances, providing these mixing channels as deeper channel portions permits such narrowing, without increasing the level of resistance across the length of that mixing channel portion.

Figure 5B:
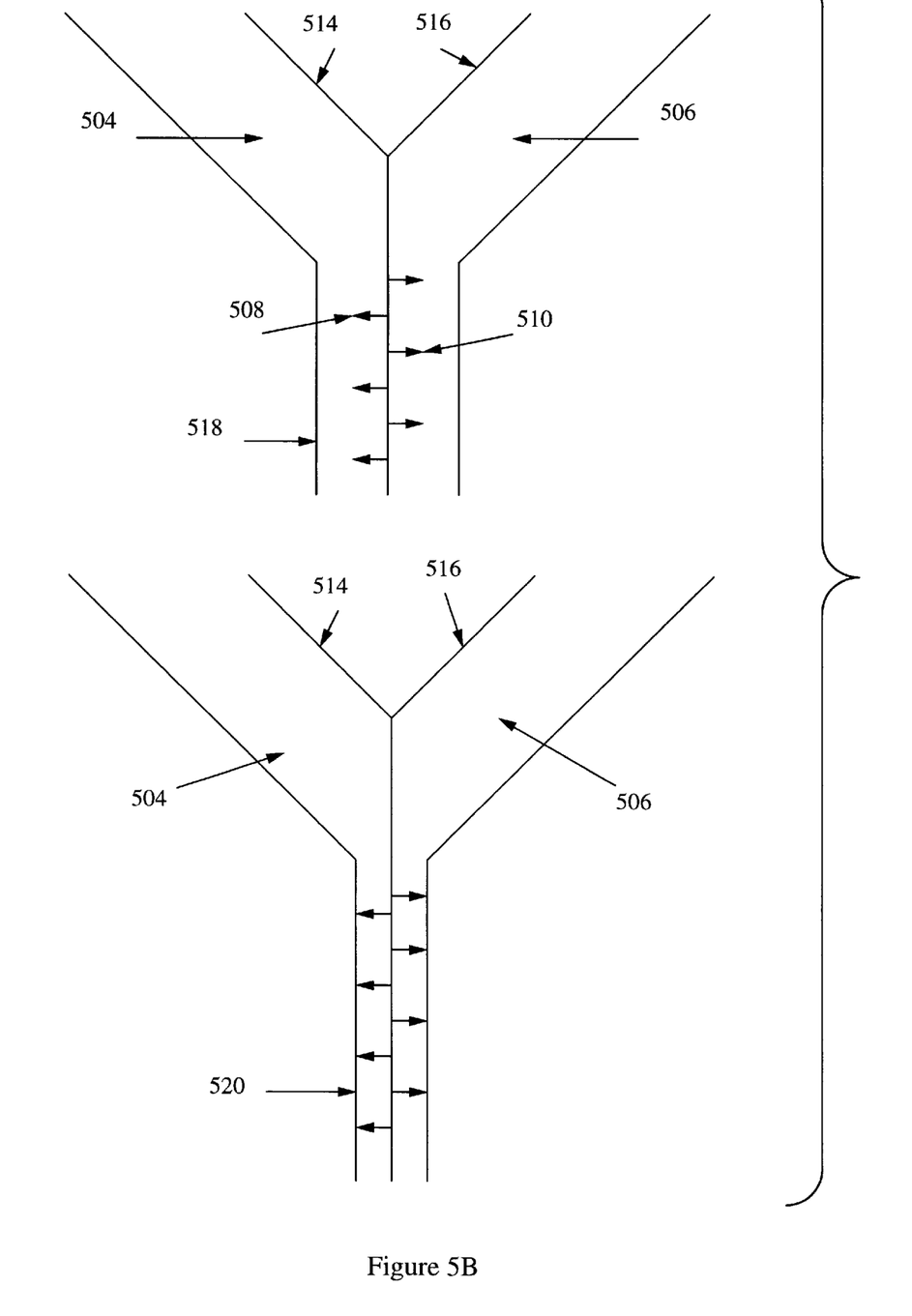

FIG 5B provides schematic illustration of a deep mixing channel, e.g., having an aspect ratio as described herein, where materials that are to be mixed are introduced in parallel. As shown in the top panel, channels 514 and 516 intersect in main channel 518. The materials to be mixed, 504 and 506, are concomitantly introduced into main channel 518 from channels 514 and 516, respectively. Again, the diffusion kinetics of the materials are illustrated by arrows 508 and 510. As illustrated in the bottom panel, channels 514 and 516 intersect a narrower and deeper channel portion 520. In this narrower/deeper channel portion 520, materials 504 and 506 mix much more quickly as a result of the same diffusion kinetics (arrows 508 and 510). Typically, this deeper/narrower channel portion will have an aspect ratio as described above, e.g., less than 1 (width/depth). By providing at least the mixing channel portion with an aspect ratio in accordance with the present invention, one achieves not only the advantages of reducing the distance molecules must diffuse, but also maintains a suitable cross-sectional area of the channel, e.g., as compared with typical channels having aspect ratios much greater than 1. This allows a narrowing of the mixing channel while allowing control or maintenance of the electrical resistance of the channel, as described above.

In addition to the above described advantages of enhanced mixing, unaltered channel resistance, use of less substrate area, and the like, such narrower deeper channels also provide for the same level of resolution as channels having the inverse aspect ratio. In particular, simply narrowing a channel to achieve enhanced mixing would result in a spreading of discrete species bands or plugs disposed in that channel, resulting in lower resolution detection of those bands. However, because the channels described herein are deeper, in addition to being narrower, the species bands do not spread, and no loss of resolution is observed. Further, detection optics in microfluidic systems typically look through (perpendicular to) the plane of the substrate in order to detect signals in a given channel. In doing so, these optics are typically directed at a portion of the channel in which detection is desired. In the case of microfluidic devices incorporating channel aspect ratios described herein, however, such deeper narrower channels permit the analysis by the detection optics, of greater numbers of detectable molecules, e.g., labeling groups, by looking through the deeper, but narrower dimension of the channel.

As noted, the improved mixing kinetics created by the devices of present invention, provide substantially improved mixing in smaller substrate areas. Further, such improved mixing permits a time-based approach to mixing and opposed to a volume-based approach. Specifically, in previous methods, mixing or dilution of one material with another is carried out by delivering different volumes of the materials to a common chamber or channel, simultaneously, in order to allow maximal mixing of these materials. In the microfluidic devices of the present invention, optimal mixing is provided by increasing the mixing channels depth. As such, materials can be combined at a preselected ratio, by transporting each material into the mixing channel, serially, and at full strength. The relative ratio of one material to the other is dictated by the amount of time each material is transported into the mixing channel, and the flow rate at which each material is transported into that channel. For example, assuming each material has an equivalent flow rate, the concentration ratio of one material to the other is directly proportional to the time each material was pumped into the common channel. Because these mixing channels have enhanced mixing characteristics, the serially introduced materials are capable of substantially completely mixing, in shorter channel lengths.

The dimensions of the mixing channel will typically vary depending upon the nature of the materials to be mixed. Specifically, larger molecules are slower to diffuse, and thus require a mixing channel that has either a greater length, or a greater cross-sectional area, such that the materials are substantially mixed while they are within the mixing channel. Typically, the dimensions of a mixing channel will fall within the range of dimensions for the microscale channels, described above. However, such channels will typically have an aspect ratio of less than 1, and preferably, less than or equal to 0.5, e.g., more than twice as deep as wide, more preferably, less than or equal to about 0.3, still more preferably, less than or equal to about 0.25, or less than or equal to about 0.2, and often in the range of about 0.1 to 0.05.. In preferred instances, these mixing channel portions will have dimensions in the range of from about 2 to about 50 $\mu$m wide, while being from about 10 to about 200 $\mu$m deep. In particularly referred aspects, the mixing channels will be from about 5 to about 20 $\mu$m wide, and from about 50 to about 200 $\mu$m deep. While mixing channels can incorporate wide regions as opposed to deep regions, such wider regions occupy greater amounts of substrate area, and as such, are less preferred. In any event, mixing channel portions will typically range from about 0.1 to about 10 $\mu$m in length, and are preferably in the range of from about 0.1 to about 3 mm in length Although the present invention has been described in some detail by way of illustration and example for purposes of clarity and understanding, it will be apparent that certain changes and modifications may be practiced within the scope of the appended claims. All publications, patents and patent applications referenced herein are hereby incorporated by reference in their entirety for all purposes as if each such publication, patent or patent application had been individually indicated to be incorporated by reference.

What is claimed is:

1. A mirofluidic device comprising a body structure and at least a first microscale channel disposed therein, the microscale channel comprising at least first and second ends and at least a portion of the microscale channel having an aspect ratio (width/depth) less than 1.

2. The microfluidic device of claim 1, further comprising an electrical controller operably linked to the first and second ends of the microscale channel, for applying a voltage gradient between the first and second ends.

3. The microfluidic device of claim 1, further comprising first and second reservoirs disposed in the body structure, the first and second reservoirs being in fluid communication with the first and second ends of the first microscale channel, respectively.

4. The microfluidic device of claim 1, wherein the microscale channel comprises at least one turn of at least 30°.

5. The microfluidic device of claim 1, wherein the microscale channel comprises at least one turn of at least 45°.

6. The microfluidic device of claim 1, wherein the microscale channel comprises at least one turn of at least 90°.

7. The microfluidic device of claim 6, wherein the microscale channel comprises at least two turns of at least 90°.

8. The microfluidic device of claim 1, wherein the microscale channel comprises at least one turn of at least 150°.

9. The microfluidic device of claim 8, wherein the microscale channel comprises at least two turns of at least 150°.

10. The microfluidic device of claim 1, wherein the microscale channel comprises at least one turn of about 180°.

11. The microfluidic device of claim 1, wherein the microscale channel comprises an aspect ratio less than or equal to about 0.5.

12. The microfluidic device of claim 1, wherein the microscale channel comprises an aspect ratio less than 0.2.

13. The microfluidic device of claim 1, wherein the microscale channel comprises an aspect ratio less than 0.1.

14. The microfluidic device of claim 1, wherein the at least one channel comprises a separation matrix disposed therein.

15. The microfluidic device of claim 14, wherein the separation matrix comprises an acrylamide polymer.

16. The microfluidic device of claim 14, wherein the separation matrix comprises a polymethylacrylamide polymer.

17. The microfluidic device of claim 1, further comprising at least a second microscale channel having first and second ends, the second microscale channel intersecting and in fluid communication with the first microscale channel.

18. The microfluidic device of claim 17, wherein the second microscale channel is in fluid communication with the first microscale channel at the second end of the second microscale channel.

19. The microfluidic device of claim 18, further comprising at least first, second and third reservoirs disposed in the body structure, the first and second reservoirs being in separate fluid communication with the first and second ends of the first microscale channel, respectively, and the third reservoir being in fluid communication with the first end of the second microscale channel.

20. The microfluidic device of claim 19, further comprising an electrical controller operably linked to each of the first, second and third reservoirs, the controller being capable of concomitantly delivering a voltage to each of the first, second and third reservoirs.

21. The microfluidic device of claim 19, further comprising a fourth reservoir disposed in the body structure, the fourth reservoir being in fluid communication with the second end of the second microscale channel.

22. The microfluidic device of claim 21, further comprising an electrical controller operably coupled to each of the first, second, third and fourth reservoirs, the controller being capable of concomitantly delivering a voltage to each of the first, second, third and fourth reservoirs.

23. The microfluidic device of claim 18, wherein the second microscale channel is in fluid communication with the first microscale channel between the first and second ends of the second microscale channel.

24. The microfluidic device of claim 1, wherein the body structure comprising the first microscale channel is fabricated from a polymeric material.

25. The microfluidic device of claim 24, wherein the body structure is injection molded from the polymeric material.

26. The microfluidic device of claim 24, wherein the first microscale channel is embossed into a polymeric substrate.

27. The microfluidic device of claim 24, wherein the polymeric material is selected from polymethylmethacrylate (PMMA), polycarbonate, polytetrafluoroethylene, polyvinylchloride (PVC), polydimethylsiloxane (PDMS) and polysulfone.

28. A microfluidic system, comprising:

a microfluidic device comprising a body structure, the body structure having at least first and second microscale channels disposed therein, each of the first and second microscale channels having first and second ends, the first microscale channel intersecting and in fluid communication with the second channel, at least the first microscale channel having an aspect ratio (width/depth) less than or equal to about 1; and an electrical control system operably coupled to the first and second ends of the first and second channels, and capable of concomitantly delivering a voltage to each of the first and second ends of the first and second channels.

29. The microfluidic system of claim 28, wherein the body structure is fabricated from a polymeric material.

30. The microfluidic device of claim 29, wherein the polymeric material is selected from polymethylmethacrylate (PMMA), polycarbonate, polytetrafluoroethylene, polyvinylchloride (PVC), polydimethylsiloxane (PDMS) and polysulfone.

31. A method of transporting at least a first material region through a microscale channel wherein the channel comprises at least one turn, the method comprising:

providing at least a portion of the channel at the turn with an aspect ratio (width/depth) that is less than 1; and transporting the first material region through the at least one turn.

32. The method of claim 31, further comprising transporting at least a second material region through the first microscale channel.

33. The method of claim 31, wherein the at least one channel comprises a separation matrix disposed therein, the first and second material regions comprise first and second species bands, separated in the at least one channel, and the step of transporting comprises applying a voltage gradient along the length of the first microscale channel.

34. The method of claim 31, wherein the step of transporting the first material region through the channel turn is carried out whereby the portion of the material region traveling at the inside edge of the channel turn traverses the turn at substantially the same rate as the portion of the material region at the outside edge of the channel turn.

35. A method of mixing a first material and at least a second material in a first microscale channel, comprising:

providing a mixing region and a non-mixing region of the first channel, the mixing region having a cross-sectional area that is sufficient to permit substantially complete diffusional mixing of the two materials while the two materials are serially transported into and through the mixing region; and serially introducing and transporting the two materials into and through the mixing region.

36. A method of mixing according to claim 35, wherein the first material and at least a second material in a microfluidic device at a preselected ratio, comprising:

introducing a first of the two materials into the mixing region at a first flow rate for a first selected time;

introducing a second of the two materials into the mixing region at the second flow rate for a second selected time, wherein the ratio of the first selected time times the first flow rate, to the second selected time times the second flow rate, is equal to the preselected ratio; and wherein the mixing channel includes a region having a cross-sectional area that is sufficient to permit substantially complete diffusional mixing of the first and second materials within the mixing channel.

37. The method of claim 36, wherein the first flow rate and second flow rate are substantially equal, and the ratio of the first selected time to the second selected time is equal to the preselected ratio.

38. The method of claim 35, wherein the mixing region of the first channel has a width equal to the non-mixing portion of the first channel and a depth that is at least twice a depth of the non-mixing region of the first channel.

39. The method of claim 35, wherein the mixing region of the first channel has an aspect ratio (width/depth) of less than 1.

40. The method of claim 35, wherein the mixing region of the first channel has an aspect ratio (width/depth) of less than about 0.5.

41. The method of claim 35, wherein the mixing region of the first channel has an aspect ratio (width/depth) of less than about 0.2.

42. The method of claim 35, wherein the mixing region of the first channel has an aspect ratio (width/depth) of less than 0.1.

* * * * *

UNITED STATES PATENT AND TRADEMARK OFFICE
CERTIFICATE OF CORRECTION

PATENT NO. : 5,842,787
DATED : December 1, 1998
INVENTOR(S) : Anne R. Kopf-Sill and J. Wallace Parce It is certified that error appears in the above-identified patent and that said Letters Patent is hereby corrected as shown below:

Claim 1, line 1, change "mirofluidic" to --microfluidic--.

Signed and Sealed this

Thirteenth Day of July, 1999

*Attest:*

Q. TODD DICKINSON

*Attesting Officer*   Acting Commissioner of Patents and Trademarks